United States Patent [19]

Mukai et al.

[11] Patent Number: 4,929,730
[45] Date of Patent: May 29, 1990

[54] BIS(1,2,5)THIADIAZOLO(3,4-B:3',4'-E) PYRAZINE, A PROCESS FOR THE PREPARATION THEREOF AND A METHOD OF USING SAME

[75] Inventors: Toshio Mukai, 1-2, Tsunogoro 2-chome, Sendai-shi, Miyagi; Yoshiro Yamashita, Miyagi, both of Japan

[73] Assignees: Fuji Xerox Co., Ltd., Tokyo; Toshio Mukai, Miyagi, both of Japan

[21] Appl. No.: 241,278

[22] Filed: Sep. 7, 1988

[30] Foreign Application Priority Data

Sep. 8, 1987 [JP] Japan .................. 62-223142

[51] Int. Cl.$^5$ .......................................... C07D 513/14
[52] U.S. Cl. .................................. 544/345; 252/500; 544/350
[58] Field of Search ........................................ 544/345

[56] References Cited

U.S. PATENT DOCUMENTS 4,478,753 10/1984 Hotta et al. ................... 260/396 N
4,500,459 2/1985 Hotta et al. .......................... 252/500

OTHER PUBLICATIONS

Y. C. Tong, Journal of Heterocyclic Chemistry, 12, 1975, pp. 451-453.
Yamashita Chem Abs 108 204598 (1988).

*Primary Examiner*—Mark L. Berch
*Attorney, Agent, or Firm*—Finnegan, Henderson, Farabow, Garrett and Dunner

[57] ABSTRACT

The compound bis[1,2,5]thiadiazolo[3,4-b:3',4'-e]pyrazine represented by the formula (I):

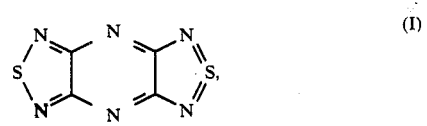

a process for preparing this compound, a method of using this compound and novel intermediate products.

1 Claim, No Drawings

BIS(1,2,5)THIADIAZOLO(3,4-B:3',4'-E) PYRAZINE, A PROCESS FOR THE PREPARATION THEREOF AND A METHOD OF USING SAME

BACKGROUND OF THE INVENTION

1. Field of the Invention

The present invention relates to a novel electron acceptor compound which is useful as an organoelectronic material, and a process for preparing the same.

2. Description of the Related Art

Tetracyanoanthraquinodimethine and derivatives thereof are known and are conventionally useful as organoelectronic materials for organic semiconductors (for example, U.S. Pat. Nos. 4,500,459 and 4,478,753). However, these materials have characteristics which make them inadequate for use as semiconductors.

SUMMARY OF THE INVENTION

The present invention provides a compound, and a method of preparing that compound, having a triple ring structure wherein heterocyclic rings are condensed onto a pyrazine ring. This compound, which was hitherto unknown, is bis[1,2,5]thiadiazolo[3,4-b:3',4'-e]pyrazine, and is represented by the following formula:

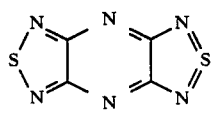  (I)

This pyrazine derivative is an electron acceptor and is useful as an organoelectronic material. Accordingly, there is provided a method of using this compound in an amount effective for use as an organoelectronic material in a semiconductor. There are also provided novel products which are obtained as intermediates in the preparation of this compound.

DETAILED DESCRIPTION

The bis[1,2,5]thiadiazolo[3,4-b:3',4'-e]pyrazine of this invention can be prepared in accordance with the reaction mechanism set forth below.

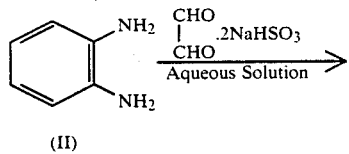

(II)

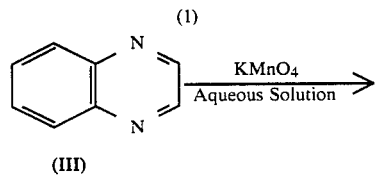

(III)

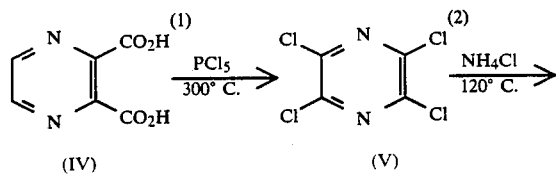

(IV)    (V)

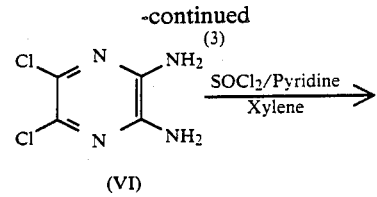

(VI)

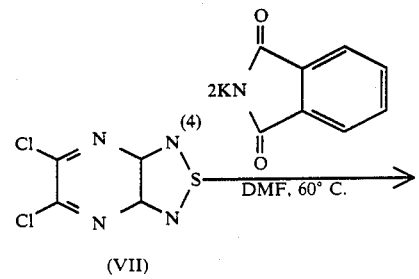

(VII)

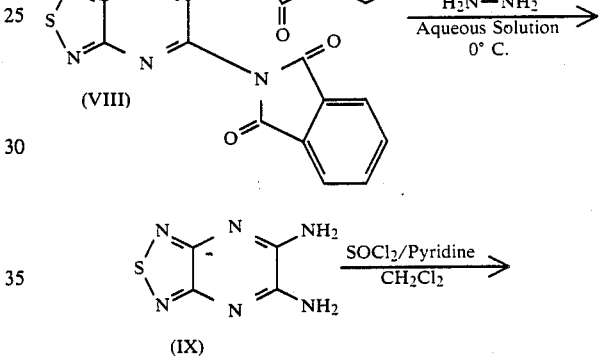

(VIII)

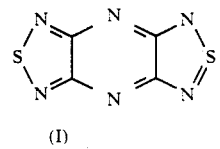

(IX)

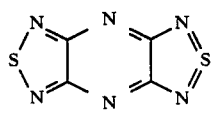

(I)

The cyclization reaction of o-diaminobenzene (compound II) in an aqueous solution of glyoxal and sodium hydrogen sulfite gives quinoxaline (compound III; See R. G. Jones et al., Org. Syn. Collective Vol. IV, page 824). Quinoxaline is in turn oxidized by an aqueous solution of potassium permanganate to produce 2,3-pyrazinedicarboxylic acid (compound IV; See R. G. Jones et al., Org. Syn. Collective Vol. IV, page 824). 2,3-pyrazinedicarboxylic acid is then chlorinated with phosphorus pentachloride at 300° C. to produce 2,3,5,6-tetrachloropyrazine (compound V; See C. G. Allison et al., J. Chem. Soc. (C), 1970, page 1023). The reaction of 2,3,5,6-tetrachloropyrazine with ammonium chloride at a temperature of 120° C. gives 2,3-diamino-5,6-dichloropyrazine (compound VI; See Palamidess et al., Ed. Sc. XXI-fasc, 11, 1966, page 810). The cyclization reaction of 2,3-diamino-5,6-dichloropyrazine with thionyl chloride in the presence of pyridine in xylene produces 5,6-dichloro-[1,2,5]thiadiazolo[3,4-b]pyrazine (compound VII; See Y. C. Tong, J. Heterocyclic Chem., 12, 1975, page 451). The 5,6-dichloro-[1,2,5]thiadiazolo[3,4-b]pyrazine is reacted with potassium phthalimide in the presence of dimethyl formamide (DMF) at a temperature of 60° C. to produce 5,6-diphthalimido[1,2,5]thiadiazolo[3,4-b]pyrazine (compound VIII; See Example 1). The 5,6-diphthalimido-[1,2,5]thiadiazolo[3,4-b]pyrazine is then reacted with an aqueous solution of hydrazine at 0° C. to produce 5,6-diamino-[1,2,5]thiadiazolo[3,4-b]pyrazine (compound IX; See Example 2). Finally the cyclization reaction of 5,6-diamino[1,2,5]thiadiazolo[3,4-b]pyrazine with thionyl chloride in the presence of pyridine in methylene chloride gives bis[1,2,5]thiadiazolo[3,4-b:3',4'-e]pyrazine (compound I; See Example 3).

5,6-di-phthalimido-(1,2,5)thiadiazolo(3,4-b)pyrazine and 5,6-diamino-(1,2,5)thiadiazolo(3,4-b)pyrazine are novel intermediate products useful for the preparation of the compound of claim 1.

The following examples are presented to provide a more complete understanding of the invention. The specific techniques, conditions, materials, preparations, and reported data set forth to illustrate the principles and practice of the invention are exemplary and should not be construed as limiting the scope of the invention.

EXAMPLE 1

Preparation of Compound (VIII) from Compound (VII)

2.0 Grams of the compound (VII) (9.7 mmol), which was prepared in accordance with the methods described in the literature above, were reacted with 4.3 grams (23.2 mmol) of potassium phthalimide and 50 ml of DMF. The reaction mixture was stirred at 60° C. for a period of 6 hours. The mixture was then cooled to room temperature, and 100 ml of water was added and thoroughly stirred. The mixture was filtered and the phthalimide precipitated out as time passed. The precipitate was washed thoroughly with water at about 50° C. and dried, whereupon 3.0 grams of the compound (VIII) was obtained in the form of a crude product consisting of cream colored crystals. These crystals were refined by recrystallization from DMF/water.

Melting point: 319°–323° C. (with decomposition).

IR (KBr): 1787, 1731, 1459, 1409, 1354, 1338, 1330, 1296, 1248, 1095, 1052, 931, 897, 874, 793, 718, and 707 cm$^{-1}$.

Mass: m/e(%) 429 (21), 428 (100, M+), 282 (17), 281 (10) 280 (16), and 104 (33).

Elemental analysis as $C_{20}H_8N_6O_4S$ Calculated: C 56.08; H 1.88; N 19.62 Found: C 55.43; H 1.64; N 19.45.

EXAMPLE 2

Preparation of Compound (IX) from Compound (VIII)

127 milligrams of the compound (VIII) (0.3 mmol) prepared in Example 1 was introduced into a 20 ml pear-shaped flask and cooled to 0° C. Five milliliters of 10% aqueous hydrazine solution at 0° C. was added to the flask and the mixture was agitated at 0° C. for a period of 3 hours and then filtered. 44 milligrams of the compound (IX) (yield 86%) was obtained as a crude product in the form of a cream colored solid. This was refined by recrystallization from ethanol.

Melting point: 312°–313° C. (with decomposition).

IR(KBr): 3400, 3330, 3250, 3090, 1673, 1660, 1620, 1590, 1530, 1485, 1336, 975, 930, 858, 800, 790, and 750 cm$^{-1}$.

Mass: m/e(%) 168 (100, M+), and 43 (31).

Elemental analysis as $C_4H_4N_6S$ Calculated: C 28.57; H 2.40; N 49.97 Found: C 37.31; H 4.21; N 37.88.

EXAMPLE 3

Preparation of Compound (I) from Compound (IX)

300 milligrams of the compound (IX) (1.8 mmol) prepared in Example 2, 3 ml of anhydrous methylene chloride and 1 ml of pyridine were placed in a 20 ml pear-shaped flask. A solution obtained by dissolving 0.4 ml (622 mg, 5.6 mmol) of thionyl chloride in 3 ml of anhydrous methylene chloride was introduced into a dropping tube and fitted to the flask. The thionyl chloride solution was drip fed into the flask slowly while agitating the mixture at room temperature and a red solid precipitated out. The mixture was further agitated for a period of 30 minutes at room temperature after the drop-wise addition had been completed. The mixture was filtered, and 177 mg (yield 51%) of crude product was obtained in the form of a red solid. This was refined by sublimation and 165 mg (yield 47%) of bis[1,2,5]-thiadiazolo[3,4-b:3',4'-e]pyrazine of formula (I) was obtained in the form of red crystals.

Melting point: 323°–329° C. (with decomposition).

IR(KBr): 1480, 1322, 1285, 1251, 960, 932, 925, and 837 cm$^{-1}$.

Mass: m/e(%) 196 (100, M+), and 46 (15).

Elemental analysis as $C_4N_6S_2$ Calculated: C 24.49; N 42.83; S 32.68 Found: C 24.45; N 42.88; S 32.81.

UV: λmax $CH_2Cl_2$/nm (ε) 421 (2.50×10$^3$), 372 (3.34×10$^4$) and 365 (2.91×10$^4$).

Having thus described the invention in detail it will be understood that further changes and modifications thereto falling within the scope of the invention as defined by the appended claims may suggest themselves to one skilled in the art.

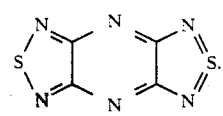

We claim:

1. A compound having the formula (I):